US006472036B2

(12) United States Patent
Saint-Ramon et al.

(10) Patent No.: US 6,472,036 B2
(45) Date of Patent: Oct. 29, 2002

(54) STRAW WITH TWO-PART PLUG

(75) Inventors: Jean-Gérard Saint-Ramon, L'Aigle (FR); Christian Beau, Voisins-le-Bretonneux (FR)

(73) Assignee: IMV Technologies (FR)

(*) Notice: Subject to any disclaimer, the term of this patent is extended or adjusted under 35 U.S.C. 154(b) by 34 days.

This patent is subject to a terminal disclaimer.

(21) Appl. No.: 09/735,089

(22) Filed: Dec. 12, 2000

(65) Prior Publication Data

US 2001/0014376 A1 Aug. 16, 2001

Related U.S. Application Data

(63) Continuation of application No. 09/198,016, filed on Nov. 23, 1998, now abandoned.

(30) Foreign Application Priority Data

Nov. 24, 1997 (FR) ........................................... 97 14729

(51) Int. Cl.[7] ................................................ C12M 1/00

(52) U.S. Cl. .................. 428/36.9; 428/36.91; 422/100; 435/287.7; 435/288.1; 435/307.1

(58) Field of Search ............................ 428/36.9, 36.91; 435/307.1, 287.7, 287.1, 288.1; 422/100

(56) References Cited

U.S. PATENT DOCUMENTS

| | | | | | |
|---|---|---|---|---|---|
| 4,558,014 | A | * | 12/1985 | Hirschfeld et al. | 250/227.11 |
| 5,190,880 | A | * | 3/1993 | Cassou et al. | 422/102 |
| 5,283,170 | A | * | 2/1994 | Cassou et al. | 422/1 |
| 5,582,602 | A | * | 12/1996 | Cassou et al. | 604/319 |
| 6,117,394 | A | * | 9/2000 | Smith | 422/100 |
| 6,145,688 | A | * | 11/2000 | Smith | 215/278 |
| 6,300,125 | B1 | * | 10/2001 | Saint-Ramon et al. | 435/287.7 |

* cited by examiner

*Primary Examiner*—Rene Dye
(74) *Attorney, Agent, or Firm*—Morgan & Finnegan, L.L.P.

(57) ABSTRACT

A straw for the conservation of small quantities of substances, notably biological substances, comprising a segment of tube fitted internally at one end with closure means comprising a two-part plug comprising a microporous and hydrophobic membrane and an insert through which there is a substantially coaxial orifice.

23 Claims, 2 Drawing Sheets

FIG. 6 bis

STRAW WITH TWO-PART PLUG

This application is a continuation of Ser. No. 09/198,016 filed Nov. 23, 1998, now abandoned.

BACKGROUND OF THE INVENTION

1. Field of the Invention

The invention relates to a straw for the conservation of small quantities of substances, notably biological substances, in particular biological liquids.

2. Description of the Prior Art

This type of straw, known under the term "French straw", was disclosed for the first time in French patent No. 995 878.

The straws used up to now included a tripartite plug consisting of two pads of a fibrous substance enclosing a powder capable of being transformed in contact with a liquid into an impermeable gel or paste adhering to the wall of the tube, creating a tight stopper.

The tripartite plug straws we have developed and marketed give entire satisfaction. Nevertheless, a certain absorption of liquid contained in the straw may have been found, although very low.

There are also smaller tripartite plugs, but this solution does not solve the absorption problem either.

A solution that has been proposed to mitigate the aforesaid problem is to replace the tripartite plug with a ball of rigid plastics material or metal. This solution has not proved satisfactory because, although the absorption of liquid contained in the straw was reduced to zero, new unacceptable difficulties arose, the stopper no longer being at all impermeable to liquids.

One aim of the invention is to provide a straw incorporating closure means which, whilst being impermeable to liquids and permeable to gases, does not absorb any quantity of liquid.

Another aim of the present invention is to provide a straw allowing liquid to be absorbed through the closure means in a short time.

SUMMARY OF THE INVENTION

The invention achieves the above aims and provides a straw for the conservation of small quantities of substances, notably biological substances, comprising a segment of tube fitted internally at one end with closure means comprising a two-part plug comprising a microporous hydrophobic membrane and an insert through which there is a substantially coaxial orifice.

The insert is usually made of a material selected from elastomer materials, thermoplastics materials and thermoplastics elastomer materials.

In a preferred embodiment of the invention the insert has a substantially cylindrical external shape.

In one arrangement in accordance with the present invention the insert is tubular and its substantially coaxial orifice can be substantially cylindrical, conical or biconical, for example.

In one embodiment of the present invention the membrane surrounds the insert over some or all of its length.

In another embodiment of the present invention the membrane is substantially perpendicular to the longitudinal axis of the insert.

In a further embodiment of the present invention the insert is a two-part insert.

The insert can equally be molded, glued or welded to the membrane.

To facilitate its insertion into the straw the insert can have rounded ends.

The insert advantageously has a sealing segment on its external wall.

The microporous membrane used in the present invention preferably has a pore diameter in the range approximately 0.001 $\mu$m to approximately 10 $\mu$m and the diameter of the pores of the membrane is more preferably less than or equal to 0.2 $\mu$m.

The membrane is made of a polymer material, for example, a material chosen from high-density polyethylene (PE-HD), polyamides, nitrocellulose, polyesters, phenol-formol resins (PF resins), perfluoroalkoxy resins (PFA resins) and fluorocarbon resins.

The polymer material of the membrane advantageously has a bubble point P greater than $6.10^5$ Pa (6 bars) for 0.2 $\mu$m.

The stopper of the straw of the present invention does not absorb liquids. It is permeable only to gases, in particular air, and is impermeable to liquids up to its intrusion pressure.

The other end of the straw, that is to say that not corporating the plug in accordance with the invention, normally remains open for filling it with the product to be conserved, which is generally a liquid.

To protect the product from contamination the open end is closed, for example welded closed, in particular by ultrasound or thermal welding, or using any other appropriate technique known to the skilled person.

Apart from the fact that it does not cause any absorption of the liquid contained in the straw, the plug of the invention has many advantages: it is not toxic, it can be sterilized and it can be frozen or heated without damage.

The plug of the invention is impermeable to liquids. It does not absorb either the diluent or the spermatozoids.

One advantage of the straw plug in accordance with the present invention is that it enables rapid filling of the straw.

The plug of the invention is particularly advantageous because it enables removal of only some of the liquid contained in the straw whilst conserving the straw for subsequent use. This has not been possible with the prior art tripartite plug.

Another advantage of the invention is that the non-absorbent plug authorizes good adhesion to the parts of the straw, so avoiding the loosening that is well known when the tripartite plug is used.

Another advantage of the invention is that, because of its porosity, the plug has a filter effect enabling use in a more or less sterile manner.

Another advantage of the invention is that the product can be re-absorbed with the same straw.

Another advantage of the two-part plug of the present invention is that the straw can be marked by the color of the insert. This provides a "color code" without having to use colored straws.

The present invention will be described in more detail with reference to FIGS. 1 through 9 of the accompanying drawings.

DETAILED DESCRIPTION OF THE PREFERRED EMBODIMENTS

Figure 1:
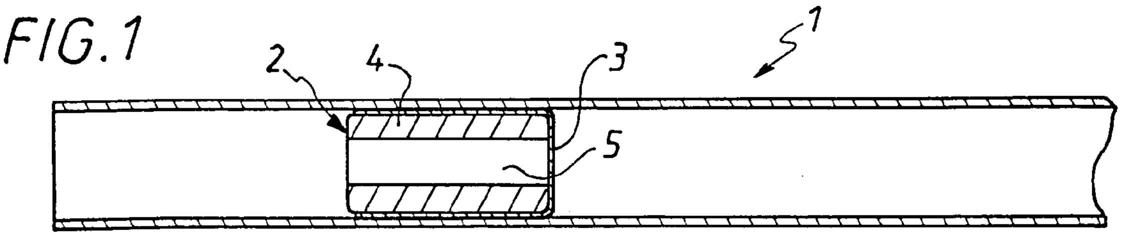
FIG. 1 is a view in longitudinal section of a straw in accordance with the invention.

FIG. 1 shows one embodiment of a straw 1 in accordance with the invention fitted with a two-part plug 2 consisting of the microporous hydrophobic membrane 3 and an insert 4 through which there is a cylindrical orifice 5.

Figure 2:
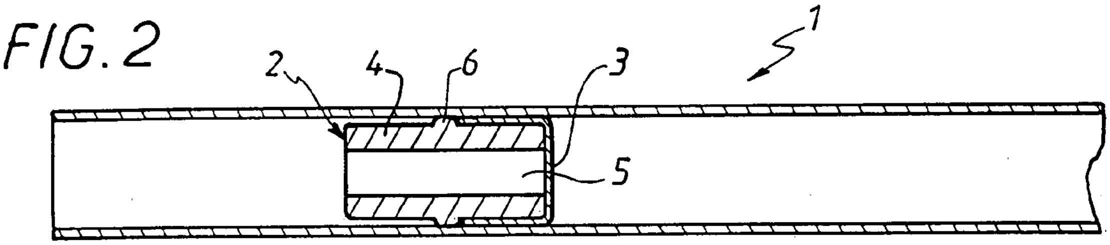
FIGS. 2 through 6 and 6 bis are views in longitudinal section showing variants of straws in accordance with the invention.

FIG. 2 shows the straw from FIG. 1 in which the insert 4 has a sealing segment 6 on its external wall.

Figure 3:
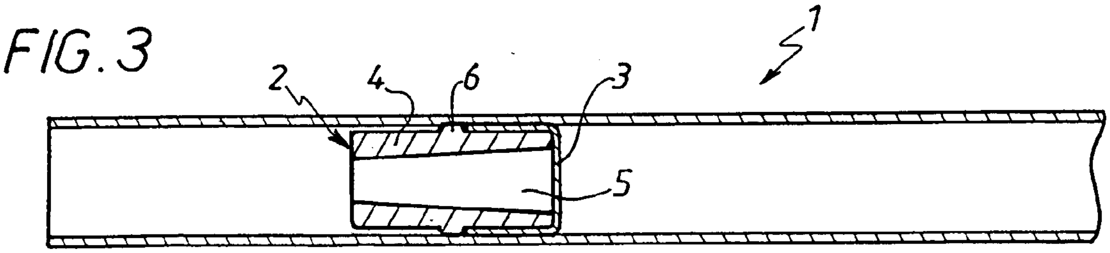

FIG. 3 shows the embodiment of the invention in which the coaxial orifice 5 is conical.

Figure 4:
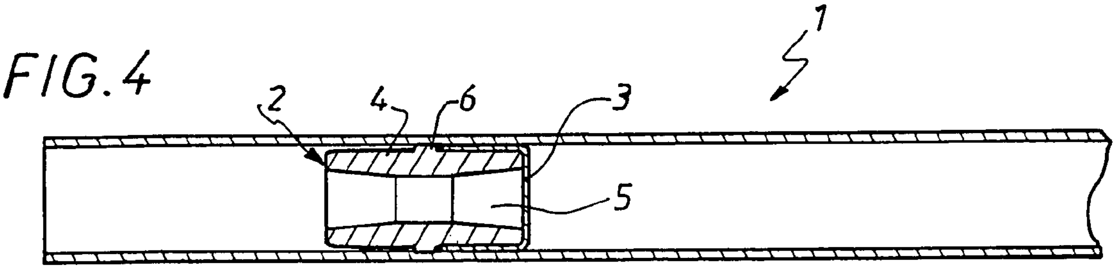

FIG. 4 shows the embodiment of the invention in which the coaxial orifice 5 is biconical.

Figure 5:
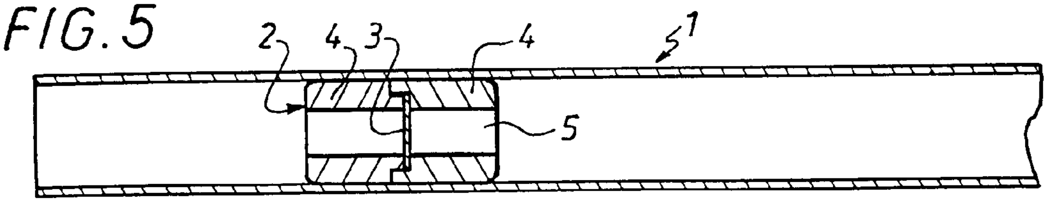

FIG. 5 shows the embodiment of the invention in which the insert 4 is a two-part insert.

Figure 6:
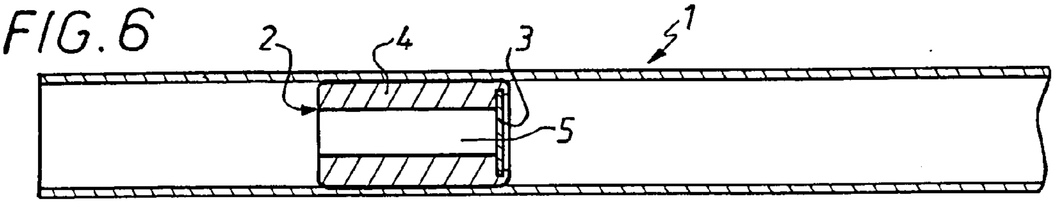
Figure 6:
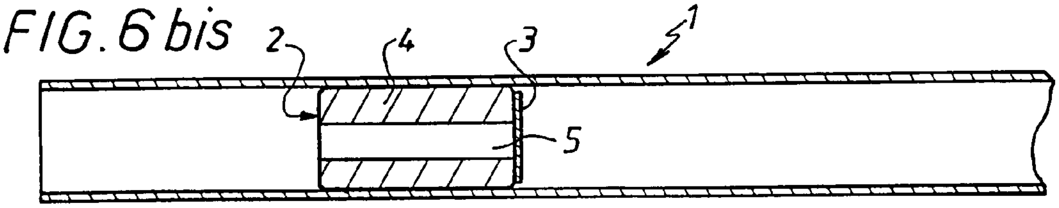

FIG. 6 shows the embodiment of the invention in which the insert 4 is molded onto the membrane 3.

FIG. 6 bis shows the embodiment of the invention in which the insert 4 is welded or glued to the membrane 3.

In the embodiment illustrated by FIG. 1 the membrane surrounds the insert 4 over its entire length.

In the embodiments illustrated by FIGS. 2 through 4 the membrane 3 surrounds the insert 4 over part of its length.

In the embodiments illustrated by FIGS. 5 and 6 the membrane 3 is substantially perpendicular to the longitudinal axis of the insert 4.

Figure 7:
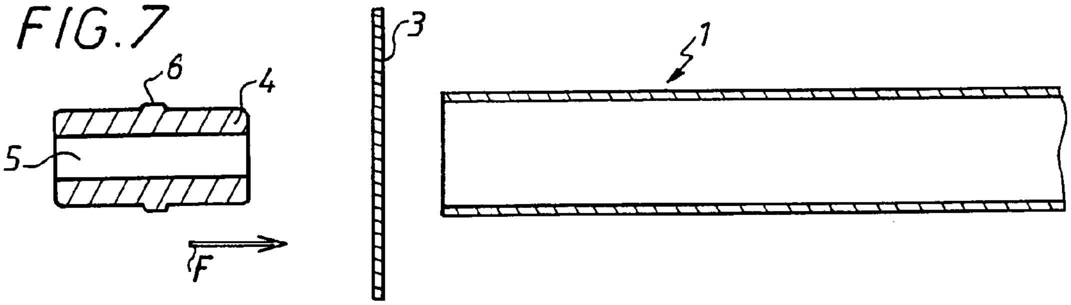
FIGS. 7 through 9 show in longitudinal section three steps of the fabrication of a straw fitted with a two-part plug in accordance with the invention.

FIG. 7 shows the "bare" straw 1', the membrane 3 and the insert 4 in accordance with the invention separated from each other.

Figure 8:
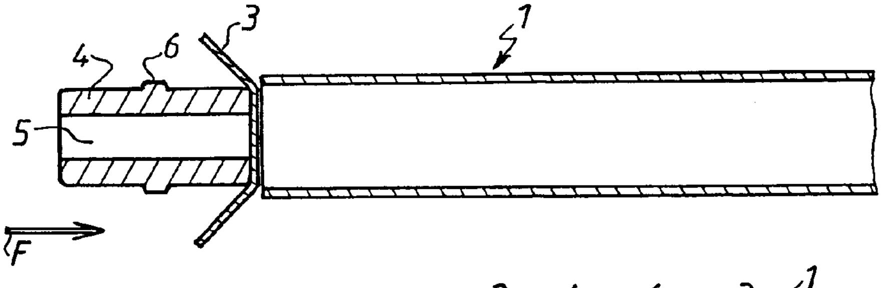

FIG. 8 shows the insert 4 onto which the membrane 3 and the straw 1' have been fitted, prior to insertion of the insert 4 with the membrane 3 into the straw 1' in the direction of the arrow F.

Figure 9:
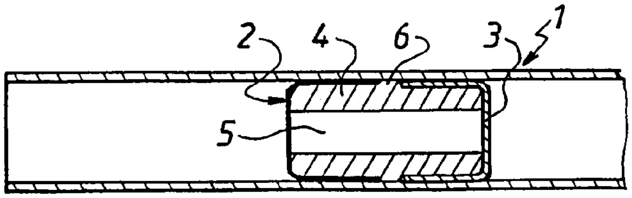

FIG. 9 shows the straw 1 incorporating the two-part plug of the present invention.

The skilled person will understand that although the invention has been described and illustrated with reference to particular embodiments, numerous variants are feasible within the scope of the invention as defined in the accompanying claims.

What is claimed is:

1. A straw for the conservation of small quantities of substances, comprising a segment of tube fitted internally at one end with closure means comprising a two-part plug comprising a microporous and hydrophobic membrane and an insert through which there is substantially coaxial orifice.

2. The straw claimed in claim 1 wherein said insert is made from a material selected from elastomer materials, thermoplastics materials and thermoplastics elastomer materials.

3. The straw claimed in claim 1 wherein said insert has a substantially cylindrical external shape.

4. The straw claimed in claim 1 wherein said insert is tubular.

5. The straw claimed in claim 4 wherein substantially coaxial orifice in said insert is substantially cylindrical.

6. The straw claimed in claim 4 wherein said substantially coaxial orifice of said insert is substantially conical.

7. The straw claimed in claim 4 wherein said substantially coaxial orifice of said insert is substantially biconical.

8. The straw claimed in claim 1 wherein said membrane surrounds said insert.

9. The straw claimed in claim 1 wherein said membrane is substantially perpendicular to a longitudinal axis of said insert.

10. The straw claimed in claim 1 wherein said insert is a two-part insert.

11. The straw claimed in claim 1 wherein said insert is molded onto said membrane.

12. The straw claimed in claim 1 wherein said insert is welded or glued to said membrane.

13. The straw claimed in claim 1 wherein said insert has rounded ends.

14. The straw claimed in claim 1 wherein said insert has a sealing segment on its external wall.

15. The straw claimed in claim 8 wherein said membrane surrounds said insert over part of its length.

16. The straw claimed in claim 8 wherein said membrane surrounds said insert over all of its length.

17. The straw claimed in claim 1 wherein said microporous membrane has a pore diameter in the range approximately 0.001 $\mu$m to approximately 10 $\mu$m.

18. The straw claimed in claim 1 wherein the pore diameter of said membrane is less than or equal to 0.2 $\mu$m.

19. The straw claimed in claim 1 wherein said membrane is made of a polymer material.

20. The straw claimed in claim 19 wherein said polymer material is selected from high-density polyethylene (PE-HD), polyamides, nitrocellulose, polyesters, phenol-formol resins (PF resins), perfluoroalkoxy resins (PFA resins) and fluorocarbon resins.

21. The straw claimed in claim 20 wherein said polymer material has a bubble point P greater than $6.10^5$ Pa (6 bars) for 0.2 $\mu$m.

22. The straw claimed in claim 1 wherein the material of said insert is colored.

23. The straw claimed in claim 1, wherein said substances are biological substances.

* * * * *